(12) United States Patent
Gattamorta

(10) Patent No.: US 6,317,887 B1
(45) Date of Patent: *Nov. 20, 2001

(54) DECORATIVE VISOR ASSEMBLY AND SECUREMENT ASSEMBLY

(76) Inventor: Ruben D. Gattamorta, Av. Rafaela y Barra , 72 4 to A, Madrid 28041 (ES)

( * ) Notice: Subject to any disclaimer, the term of this patent is extended or adjusted under 35 U.S.C. 154(b) by 0 days.

This patent is subject to a terminal disclaimer.

(21) Appl. No.: 09/613,670

(22) Filed: Jul. 11, 2000

Related U.S. Application Data

(63) Continuation-in-part of application No. 09/066,199, filed on Apr. 24, 1998, now Pat. No. 6,094,742.
(60) Provisional application No. 60/044,866, filed on Apr. 25, 1997.

(51) Int. Cl.$^7$ .................................................. A61F 9/00
(52) U.S. Cl. ................................. 2/12; 2/918; 2/DIG. 3; 2/DIG. 10
(58) Field of Search ........................... 2/12, 918, DIG. 3, 2/DIG. 10

(56) References Cited

U.S. PATENT DOCUMENTS 2,803,015 * 8/1957 Malone ........................... 2/DIG. 10

* cited by examiner

*Primary Examiner*—John J. Calvert
*Assistant Examiner*—Katherine Moran
(74) *Attorney, Agent, or Firm*—Malloy & Malloy, P.A.

(57) ABSTRACT

A decorative visor assembly to be worn in shading relation on a user's forehead, the visor assembly including a first and a second, generally planar material panels, and a seal assembly structured to selectively and precisely couple the first material panel to the second material panel. The seal assembly itself includes a perimeter seal structured to define a primary chamber between the first and the second material panels, and which is substantially fluid impervious so as to contain a quantity of a fluid within the primary chamber for selective introduction and removal so as to define an inflated orientation and a deflated orientation of the primary chamber. The seal assembly further includes a plurality of interior seals that couple the first material panel to the second material panel such that upon inflation of the primary chamber, a force of inflation is precisely and selectively translated through the first and the second material panels so as to define a forward shading region and a rear securing region. The rear securing region includes a securing assembly and is structured to be expandably coupled about the user's head so as to extend the forward shading region outwardly, in a generally perpendicular orientation from a forehead of the user in a shading relation over a user's eyes.

13 Claims, 8 Drawing Sheets

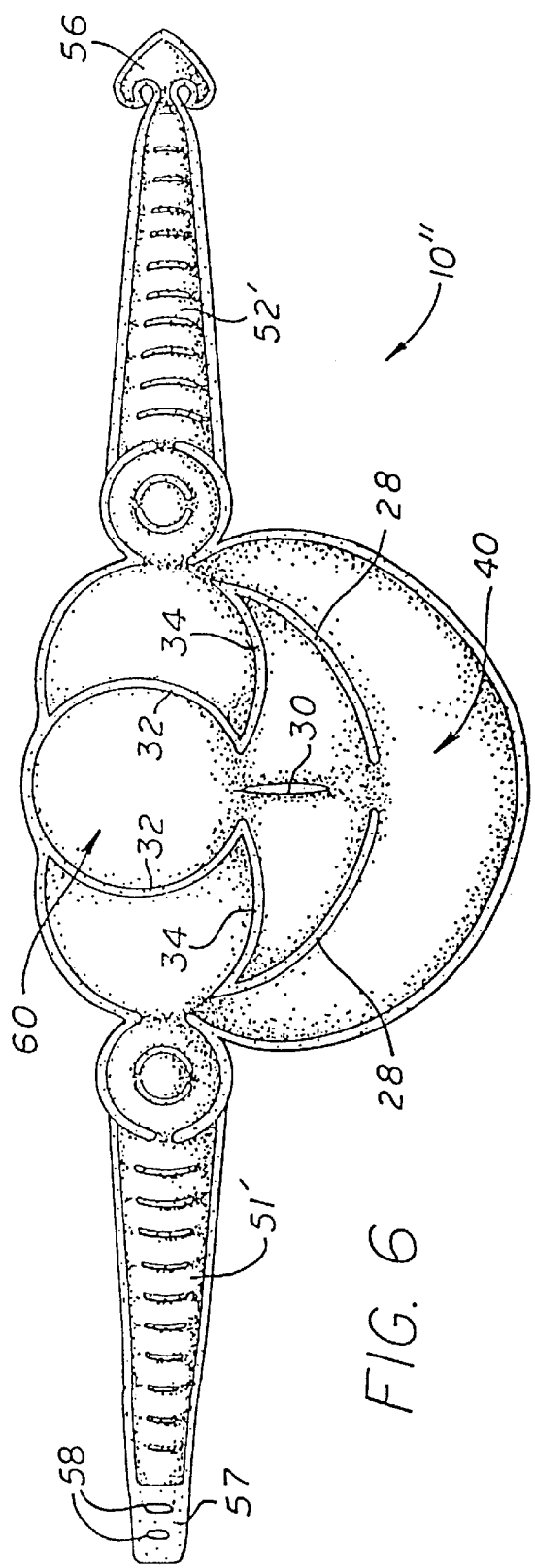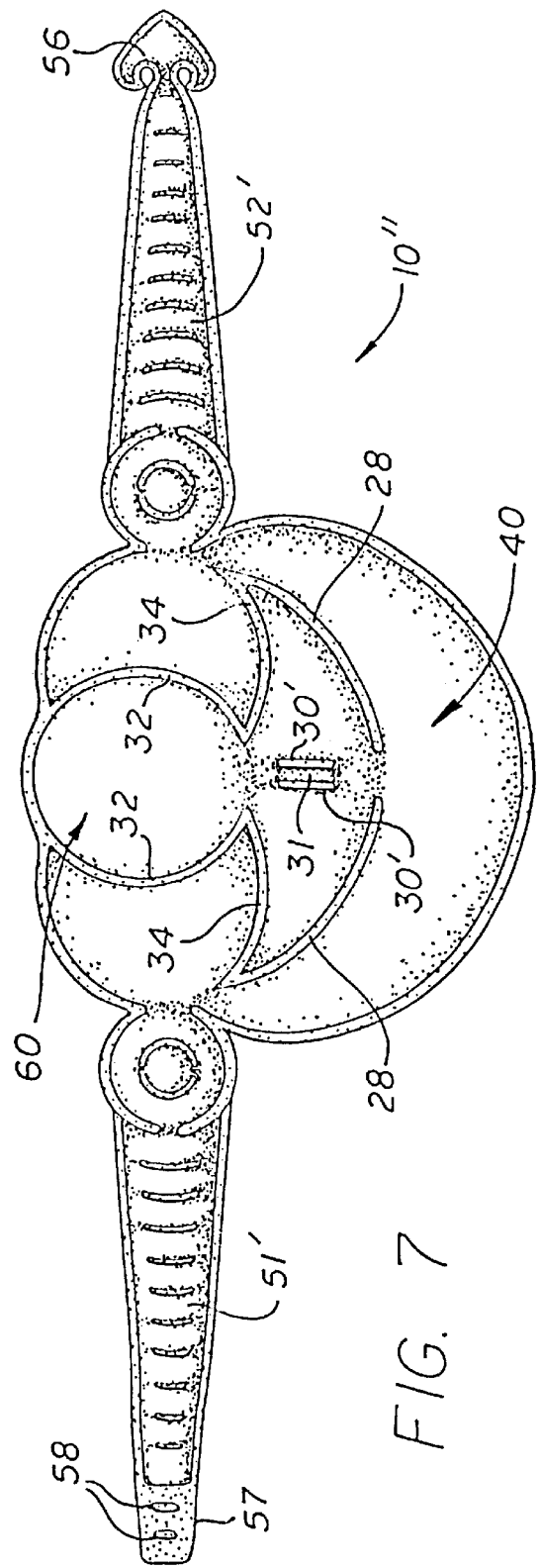

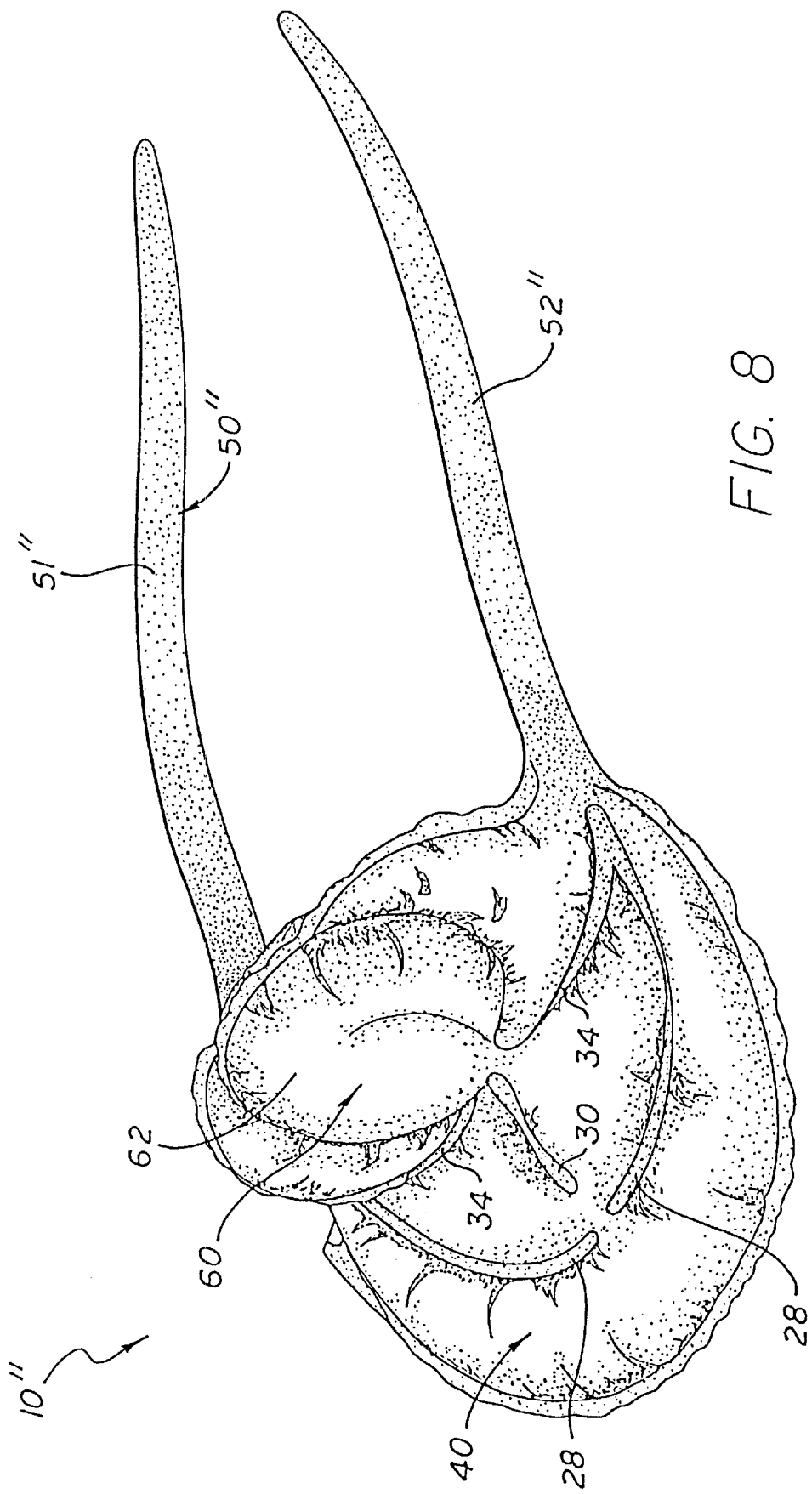

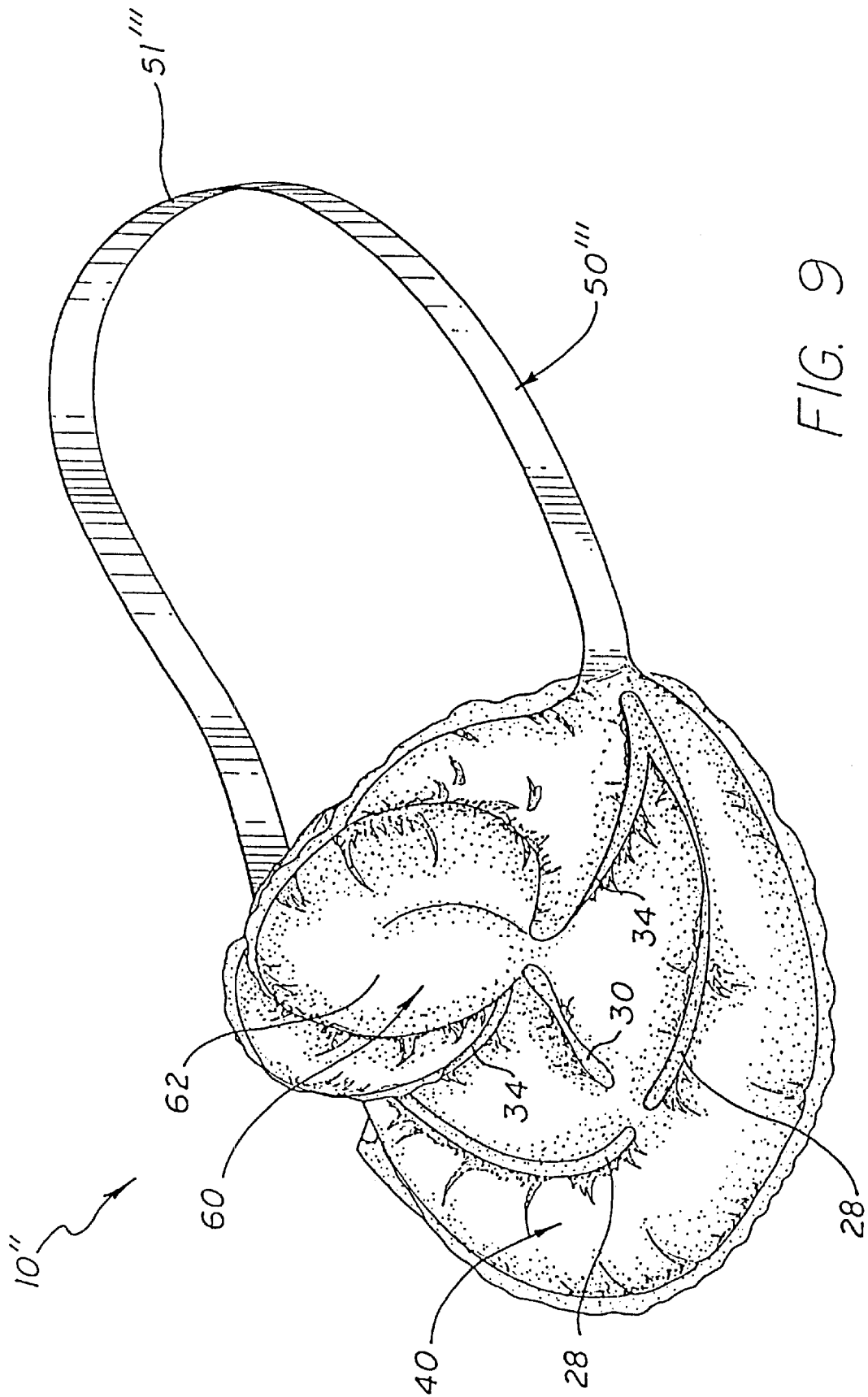

DECORATIVE VISOR ASSEMBLY AND SECUREMENT ASSEMBLY

CLAIM OF PRIORITY

The present application is a continuation-in-part patent application of previously filed, now pending application having Ser. No. 09/066,199, now U.S. Pat. No. 6,094,742, filed on Apr. 24, 1998, which was based on a claim to priority under 35 U.S.C. Section 119(e) to provisional patent application assigned Ser. No. 60/044,866, filed on Apr. 25, 1997.

BACKGROUND OF THE INVENTION

1. Field of the Invention

The present invention is directed towards a visor assembly to be worn on the forehead of the user in order to provide an attractive, lightweight and unique eye shield and decorative item to be worn, and a securement assembly that is particularly, although not exclusively, suited for adjustably securing the visor assembly around user's heads of different sizes. Moreover, the invention relates to a visor assembly that is conveniently stored and contained until use, yet which has an enhanced three dimensional appearance and a substantial, embellished shape despite its compact and storable nature.

2. Description of the Related Art

Visors are a commonly worn and utilized alternative to hats, and are frequently utilized to provide shade, adornment and/or an effective display location for a logo, advertisement or other decorative graphic. Typically, visors are formed of a similar material to that of a hat, are covered in cloth, and incorporate an elastic band to secure them to a wearer's head. Alternatively, and as is often the case in promotional situations wherein visors are distributed as an inexpensive advertising/promotional item, such as an in a park, fair or other outdoor venue wherein shielding from the sun would be favored by the consumers, more inexpensive visor assemblies are provided. In such bulk distribution situations, the visors are typically formed of a molded plastic material which is shaped in the visor form. Moreover, the natural resilient tendencies of the plastic material enable the device to be retained on the user's head. Unfortunately, however, the inexpensive visor assemblies that are presently known have very limited decorative appeal and variance, are generally rigid and cannot be conveniently and effectively stored when not in use, tend to pinch a wearer's head if worn for extended periods of time, and can be expensive to manufacture in bulk, especially due to the three dimensional molding requirements.

In addition to the basic cost associated with the manufacture of such visor assemblies in bulk, incorporating an elaborate and/or embellished design configuration is also not cost effective due to the substantial molding adaptations that must be achieved in order to make a particular visor assembly. Indeed, once a particular configuration is developed into a mold, variations therefrom are typically not utilized at all due to the expense of manufacturing a new mold. Furthermore, such conventional plastic visor designs have a very limited embellished appearance and are truly a functional item rather than an elaborate, ornate, three dimensional, festive item.

As such, it would be highly beneficial to provide an improved visor assembly which has a substantially attractive and enhanced three dimensional ornamental appearance that not only provides shielding to the eyes of a wearer, but also defines an elaborate, festive and artful article to be worn by a user. Additionally, such an improved visor assembly should be cost effective to manufacture in a variety of configurations and in a variety of different styles and attractive arrangements. Further, such a device should be substantially lightweight and comfortable to wear, and should be conveniently storable both before and after use. The assembly of the present invention provides such a configuration and overcomes the deficiencies remaining in the art relating to sun visors.

Furthermore, it is recognized that with such items to be worn on the head and/or with other items to be secured to another article, a degree of adjustability is often beneficial as the size of the head or article may vary from one use to another, and it is generally not practical to manufacture every possible size. Along these lines, it is seen that flexible, rubber band type elastic material fasteners have been used with some items. Those devices, however, are often susceptible to breakage and are usually not practical for the manufacture of the remainder of the item. As a result, the elastic band must often be fastened, such as by pins or staples to the item which it will secure in place. Alternately, and often as associated with head gear, other adjustable securement assemblies are provided whereby the adjustability is derived by the amount that one segment overlaps another, a series of clips or a hook and loop fastener structure providing for fixing of the desired sizing. Unfortunately, such structures, once sized, provide a fixed sizing unless re-adjusted. As such, if the article about which they are secured changes in size, such as due to flexing or movement, the sizing remains the same. Further, if tight securement is desired, no comfort expansion is provided. As a result, it would also be beneficial to provide a securement assembly which need not be formed from a specifically high elasticity material, but provides a degree of flexibility and adjustability in its sizing during actual use after it has been fastened in place.

SUMMARY OF THE INVENTION

The present invention relates to a decorative visor assembly to be worn on a user's head. Specifically, the visor assembly includes a first, generally planar, material panel, and a second, generally planar, material panel. Preferably, these material panels are formed of an elastic, yet flexible material, such as that typically provided under the trademark Mylar®.

Additionally, the decorative visor assembly includes a seal assembly structured to selectively and precisely couple the first material panel to the second material panel. In particular, the seal assembly includes a perimeter seal structured to define a primary chamber between the first and second material panels. Moreover, that perimeter seal is substantially fluid impervious so as to contain a quantity of a fluid, such as air, within the primary chamber.

So as to permit the selective flow of fluid into and out of the primary chamber, valve means are also provided. Specifically, the valve means enable the selective flow of the air so as to define an inflated orientation and a deflated orientation of the primary chamber defined between the first and second material panels.

Additionally, the seal assembly of the decorative visor assembly includes a plurality of interior seals. The interior seals are structured and disposed to couple the first material panel to the second material panel such that upon inflation of the primary chamber, a force of inflation resultant from the filing of the primary chamber and tension being applied to the first and second material panels is precisely and selectively translated through the first and second material panels in order to define a forward shading region and a rear securing region.

The rear securing region is structured to be coupled, at least partially, about the user's head, thereby retaining the entire visor assembly appropriately positioned on the user's head. Moreover, the rear securing region is coupled about the user's head so as to extend the forward shading region outwardly, in a generally perpendicular orientation, from a forehead of the user and in a shading relation over the user's eyes. Further, in one embodiment of a securing assembly which is illustrated in association with the visor, but may also be used with a variety of other items to secure them to a human or other article, the securement assembly is structured in such manner as to be adjustable during use. Specifically, a pair of extension segments are provided including a series of interior seals. The interior seals define chambers which when filled with a fluid provide a degree of stiffness for securement purposes, but also allow a degree of expansion and/or contraction of the extension segments for adjustability purposes.

These and other features will become apparent from the claims and the accompanying detailed description.

BRIEF DESCRIPTION OF THE DRAWINGS

For a fuller understanding of the nature of the present invention, reference should be had to the following detailed description taken in connection with the accompanying drawings in which:

FIG. 6 is a top plan view of the embodiment of FIG. 4 including the securing assembly in an un-inflated state;

FIG. 7 is a top plan view of the embodiment of FIG. 4 illustrating an alternative embodiment of a forced focused segment;

FIG. 8 is a perspective view of a further embodiment of the improved visor assembly of the present invention illustrating another embodiment of the rear securing region;

FIG. 9 is a perspective view of a further embodiment of the improved visor assembly of the present invention illustrating another embodiment of the rear securing region;

Like reference numerals refer to like parts throughout the several views of the drawings.

DETAILED DESCRIPTION OF THE PREFERRED EMBODIMENT

Figure 1:
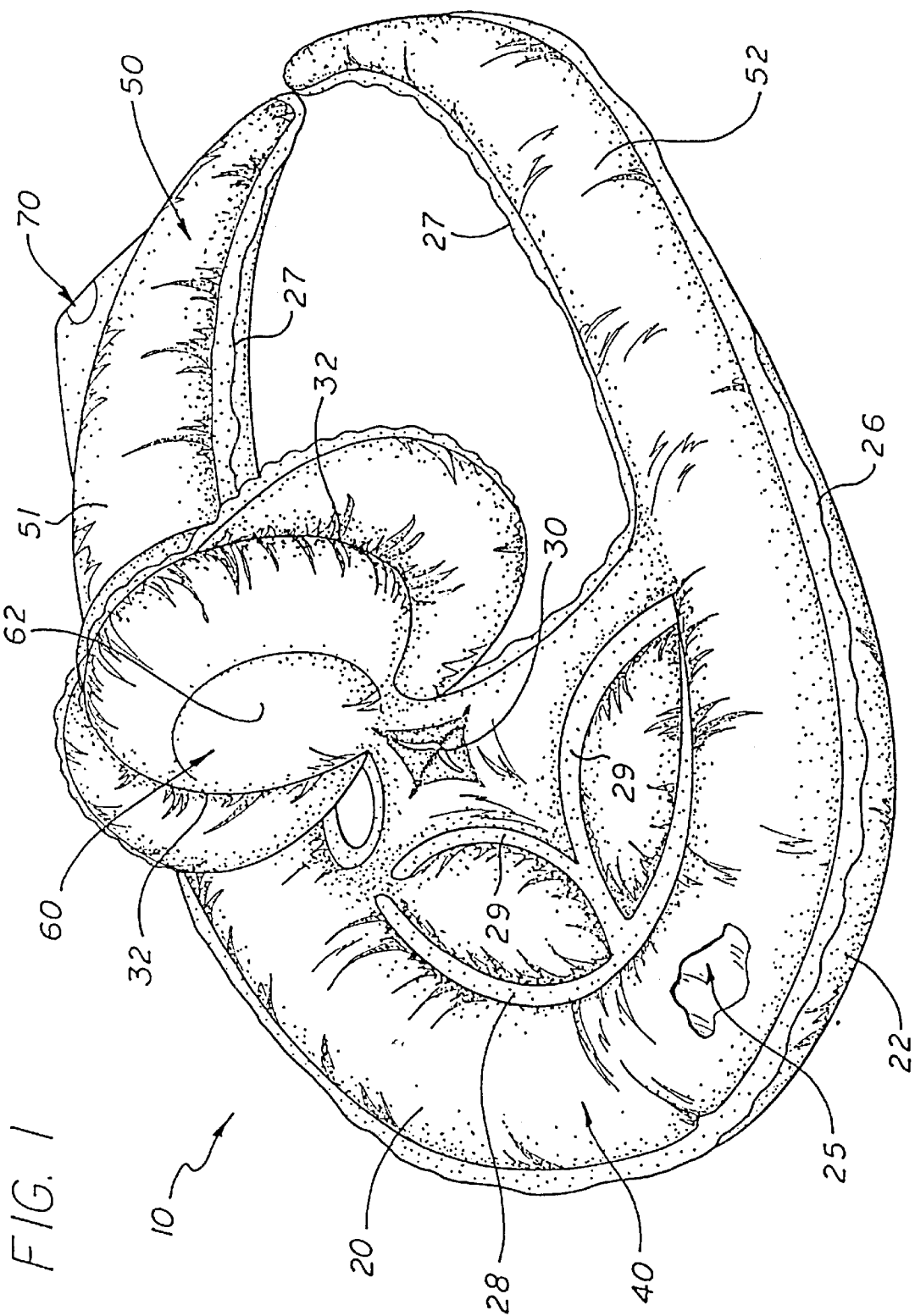
FIG. 1 is a perspective view of one embodiment of the improved visor assembly.

Shown throughout the Figures, the present invention is directed towards a decorative visor assembly, generally indicted as 10. In particular, the decorative visor assembly 10 is structured to be worn on a user's forehead, preferably in such a manner as to provide shading and coverage above the user's eyes. Moreover, the decorative visor assembly 10 includes a first, generally planar material panel 20, and a second generally planar material panel 22. In the preferred embodiment, the material panels 20 and 22 are formed of an elastic, yet flexible material such as the plastic material usually sold under the trademark MYLAR®. Moreover, the first and second material panels 20 and 22 may be provided in any of a number of different colors and/or reflective appearances, and may also be provided with decorative indicia thereover so as to substantially enhance an attractive appeal of the decorative visor assembly 10.

Additionally, the decorative visor assembly 10 of the present invention includes a seal assembly. The seal assembly is preferably denoted by a plurality of heat seals 26, 27, 28, 29, 30, 32, 34, 35, and 37, which are preferably formed directly between the first and second material panels 20 and 22. Of course, it is understood that the seals which comprise the seal assembly may be adhesive seals or may incorporate additional material segments extending between the first and second material panels 20 and 22. Still, however, as indicated the preferred embodiment includes a heat seal directly between the first and second material panels 20 and 22, thereby providing for substantial ease of manufacturing and also providing for more effective and focused distribution of forces as will be discussed subsequently.

Looking further to the seal assembly, it includes at least one perimeter seal 26 and 27 structured to define a primary chamber 25, as illustrated in FIG. 1, between the first and second material panel 20 and 22. Indeed, the perimeter seals 26 and 27 are preferably disposed about a perimeter edge of the first and second material panels 20 and 22, thereby maximizing an interior dimension of the primary chamber 25 defined therebetween. Of course, however, the first and second material panels 20 and 22 may extend beyond the perimeter seals 26 and 27 if decorative material overlapping is desired.

In order to define the primary chamber 25 in such a manner as to receive a quantity of fluid, such as preferably air, therein, the perimeter seals 26 and 27 are preferably substantially fluid impervious. As a result, as the primary chamber 25 is inflated, the air is contained therein in order to maintain a defined, inflated form of the visor assembly 10.

Furthermore, in order to permit the selective flow of fluid into and preferably out of the primary chamber 25, the decorative visor assembly further includes valve means 70. Specifically, the valve means 70 which may include any of a number of conventional valve type configurations, preferably includes a self sealing valve, such as may conventionally be utilized in a balloon or similar inflated object. Such a self sealing valve is structured to open upon the blowing of air therethrough or preferably upon the introduction of an inflation tube therethrough beyond a seal point of the valve and into the primary chamber 25.

Accordingly, through the valve means 70, the air is introduced and/or removed from the primary chamber 25, thereby defining an inflated orientation of the visor assembly 10 wherein an attractive, embellished three dimensional design is provided, or a deflated orientation of a primary chamber 25 wherein the visor assembly includes a substantially flat, foldable and conveniently storable configuration.

The seal assembly further includes a plurality of interior seals. The interior seals, which are also preferably heat seals formed directly between the first and second material panel 20 and 22 and may incorporate all or part of the perimeter seals, are disposed to couple the first material panel 20 to second material panel 22 such that upon inflation of the primary chamber 25, a force of inflation is precisely and selectively translated through the first and second material panels in order to define a forward shading region 40 and preferably a rear securing region 50. In particular, as the primary chamber 25 is inflated the first and second material panels 20 and 22 tend to be urged away from one another. As a result of the specific positioning of the interior seals, only a certain degree of separation can be achieved between the first and second material panels throughout the visor assembly. Moreover, due to the specific and precise positioning of the interior seals, as continued inflation is achieved, the outward pressure or force which is exerted on the first and second material panels 20 and 22 by the air which has been introduced and now maintains the visor assembly in an inflated orientation, is translated through the first and second material panel which pull away from some of the seals and towards other seals. It is this particular configuration and orientation of the interior seals which enables and enhances the three dimensional, ornamental configuration to be achieved by the visor assembly 10 and moreover, which functions to define the lower shading region 40, the rear securing region 50, and as will be described subsequently, a preferred upwardly depending region 60.

Looking specifically to the rear securing region 50, it is structured to be coupled at least partially about the user's head, thereby maintaining the visor assembly 10 properly positioned on the user. Moreover, the rear securing region 50 is structured such that upon being coupled about the user's head, it extends the forward shading region 40 outwardly, in a generally perpendicular orientation, from a forehead of the user, thereby positioning the forward shading region 40 in a shading relation over a user's eyes.

Figure 2:
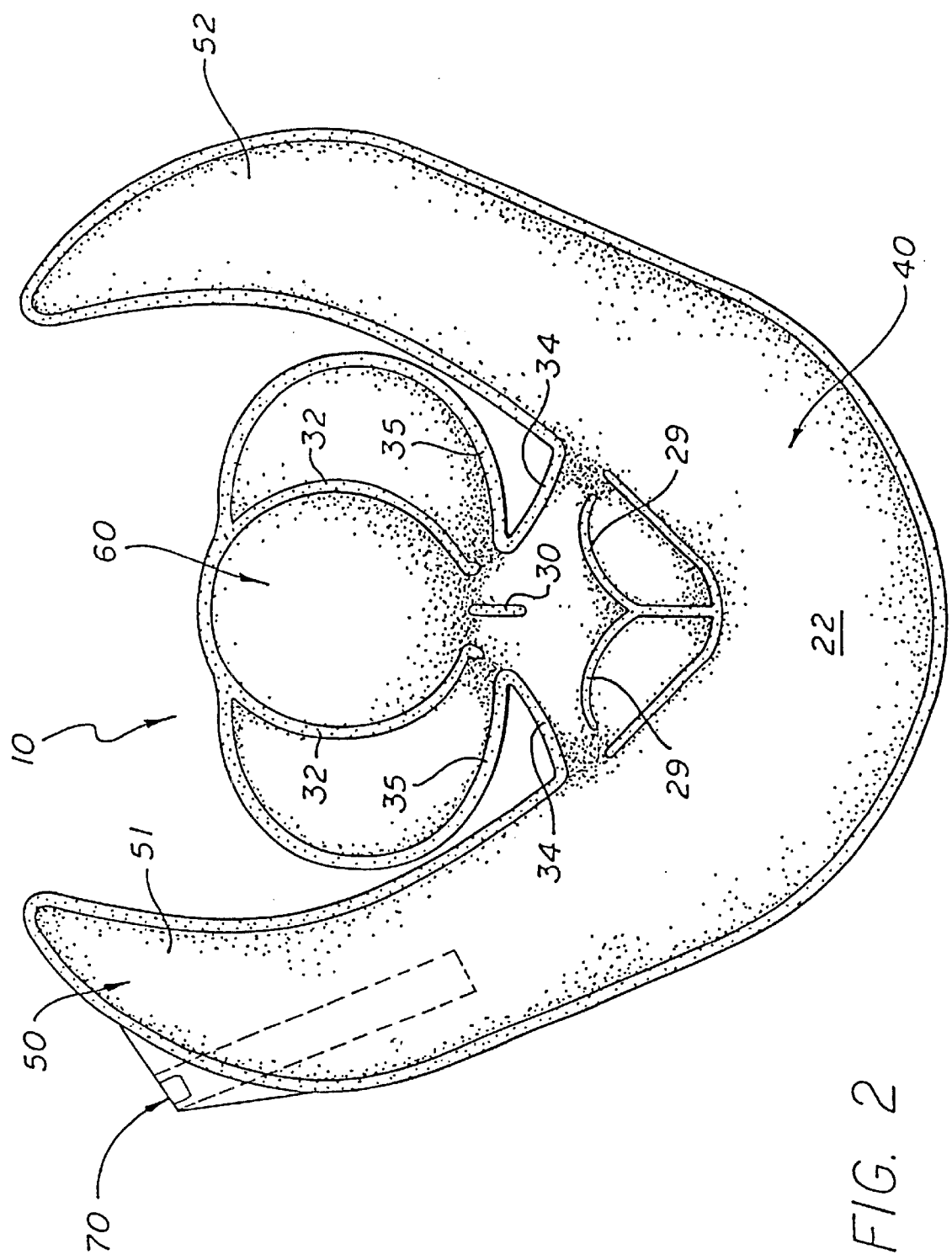
FIG. 2 is a top plan view of the visor assembly of FIG. 1 in an uninflated state.
Figure 3:
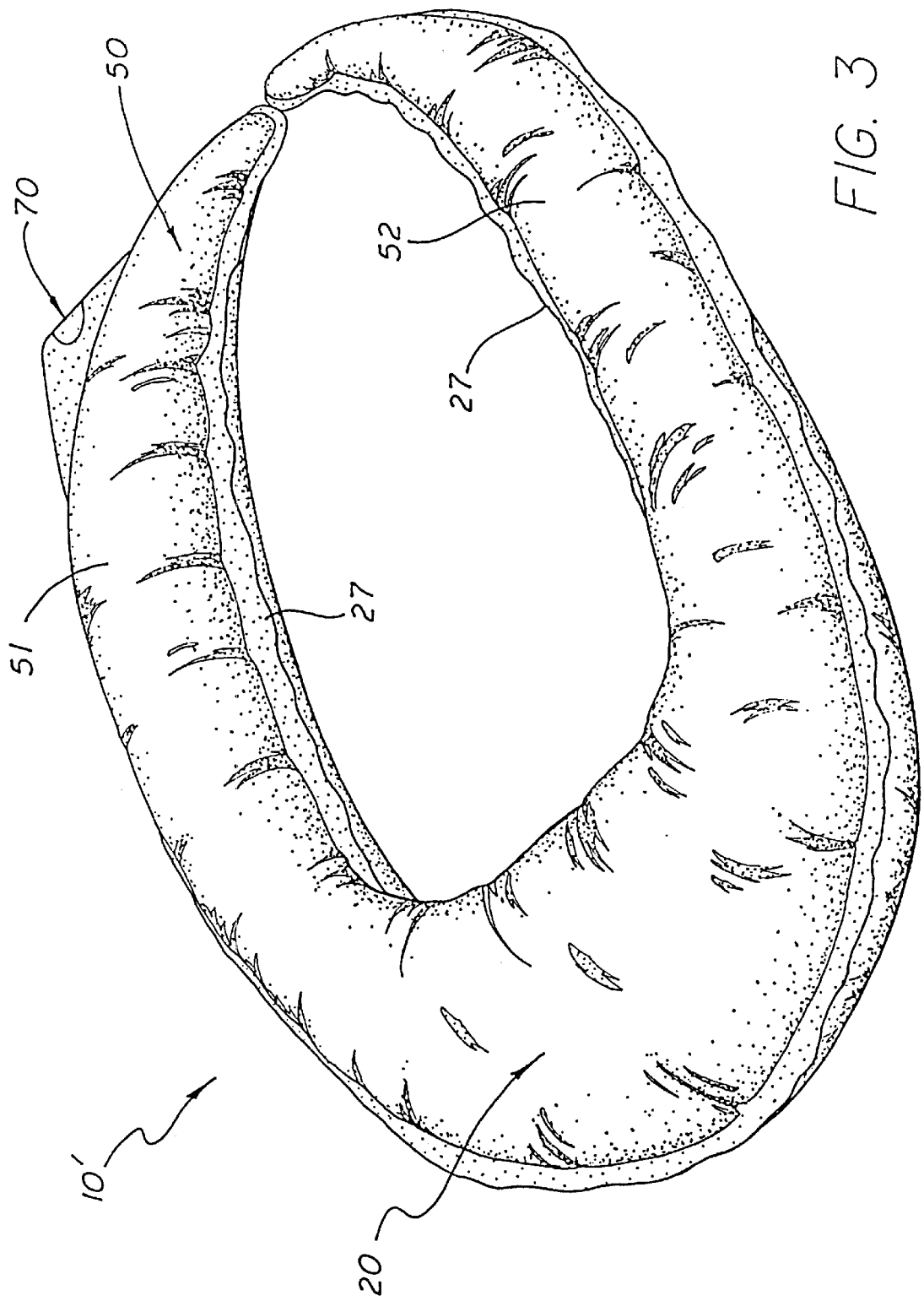
FIG. 3 is a perspective view of an alternative embodiment of the improved visor assembly.
Figure 4:
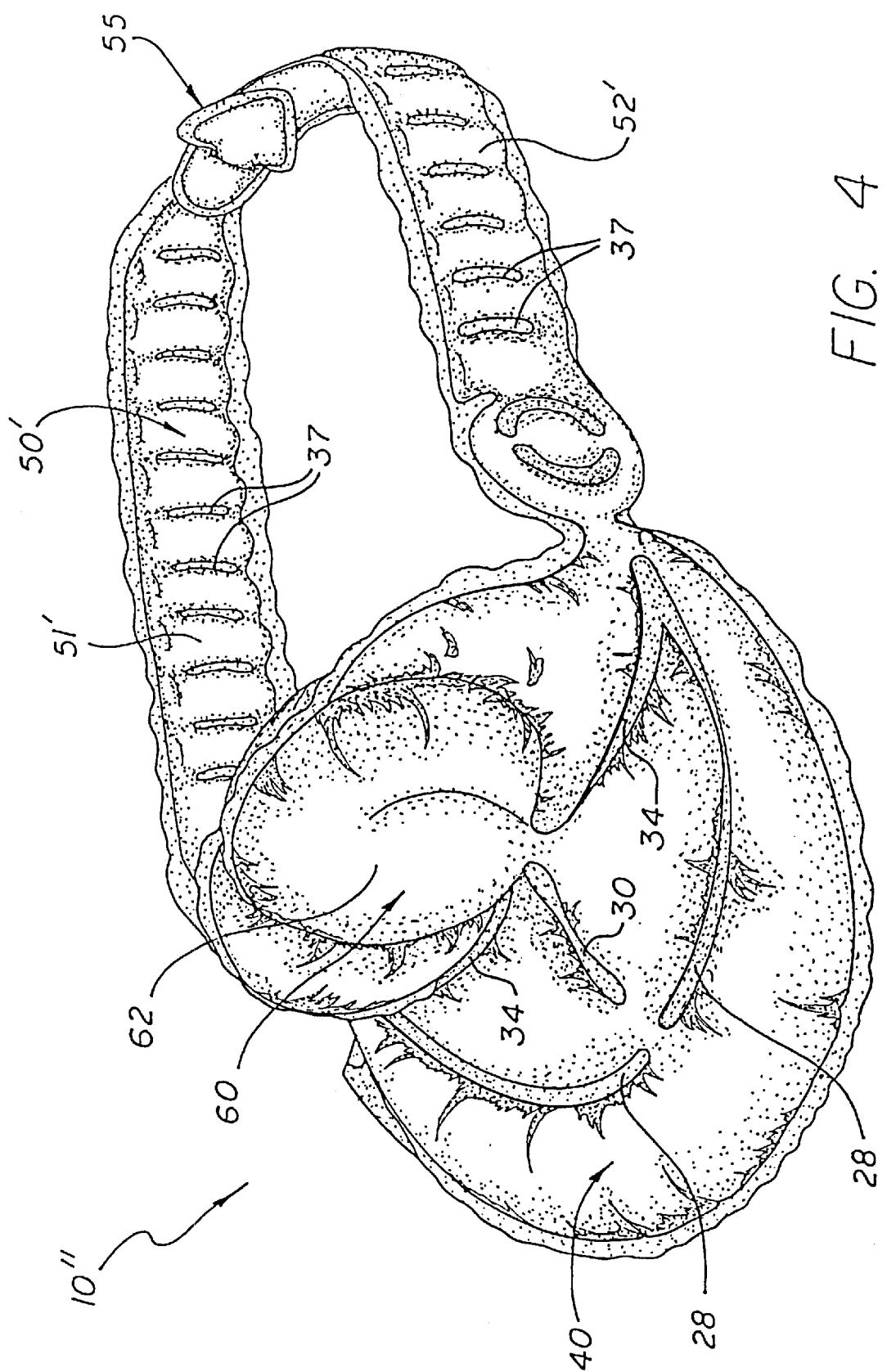
FIG. 4 is a perspective view of a further embodiment of the improved visor assembly of the present invention illustrating an embodiment of the fastening assembly of the securing assembly of the present invention in an engaged orientation in association with a decorative visor.
Figure 5:
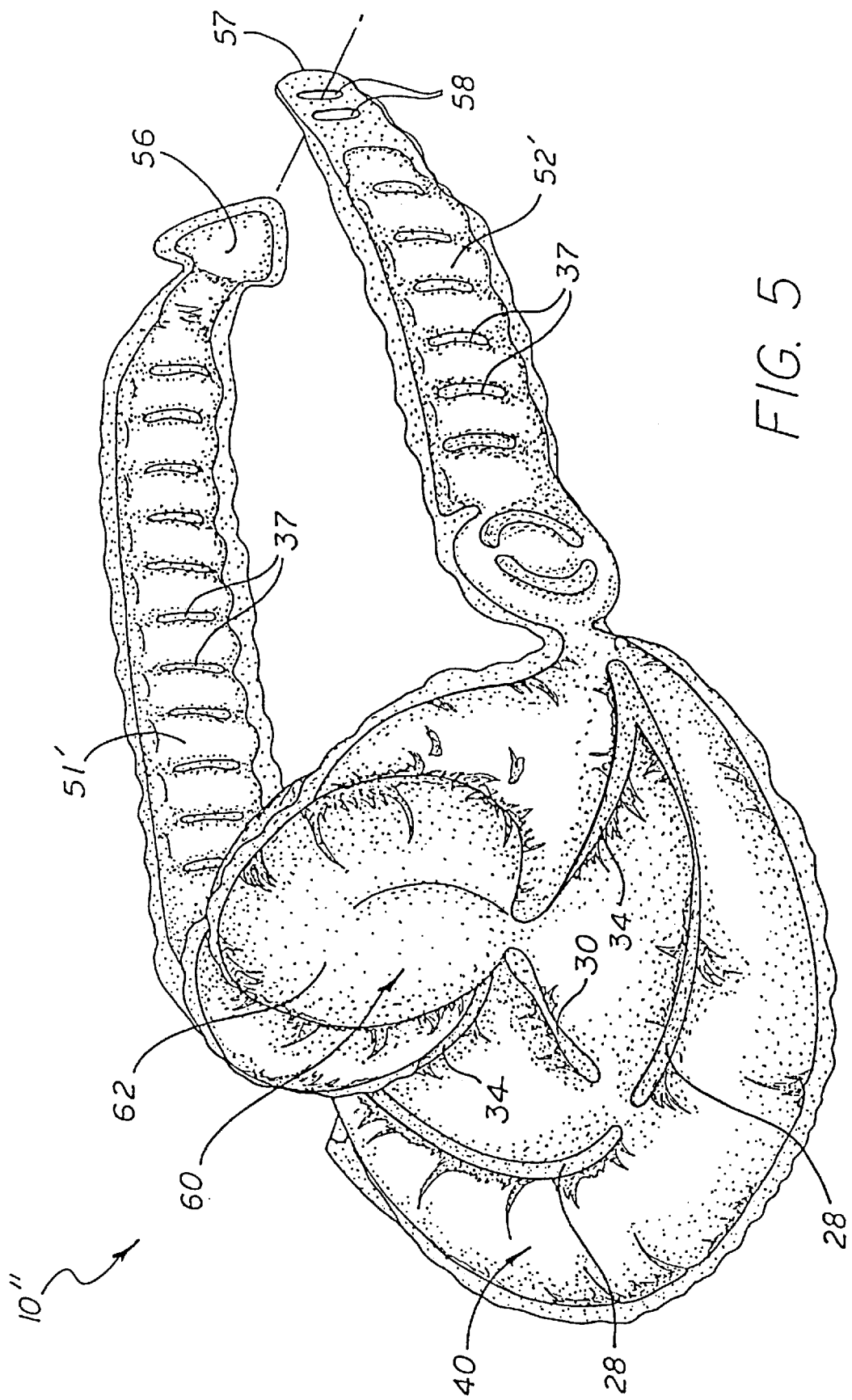
FIG. 5 is a perspective view of the securing assembly of the present invention illustrating an embodiment of the fastening assembly in an unengaged orientation.

Looking to FIGS. 1, 2 and 3, a first embodiment of the rear securing region 50 is shown. In particular, this first embodiment of the rear securing region 50 includes a pair of extensions segments 51 and 52 that are structured to extend along opposite sides of the user's head. Moreover, the interior seals 27 which define the rear securing region 50 are structured and particularly disposed in such a manner as to generally bias the extension segments 51 and 52 towards one another upon inflation of the primary chamber 25 and a corresponding translation of the force of inflation into the first and second material panel 20 and 22. Specifically, the extension segments 51 and 52 preferably provide a generally bowed configuration when inflated, and although having no biasing tendencies when the visor assembly 10 is in an un-inflated orientation, upon the primary chamber 25 being inflated into its inflated orientation, the outward tension and forces exerted by the air filing the primary chamber 25 functions to bias the extension segments 51 and 52 towards one another due to the precise configuration of the interior seals 27. Moreover, so as to further promote the general bias of the extension segments 51 and 52 towards one another, it is preferred that a forward region of the extension segments, which are generally adjacent the forward shading region 40, be generally wider than a rear region of the extension segments. It is seen that this width is translated into a larger versus a smaller cross-sectional diameter upon the primary chamber 25 being inflated. As such, it is seen that in this first embodiment of the rear securing region 50, the visor assembly 10 and 10' are effectively maintained on the user's head without requiring any extraneous fastening assemblies, such as an elastic strap.

Turning to FIGS. 4, 5, 6 and 7, an alternative embodiment of the rear securing region is shown, defining an innovative securing assembly 50'. This securing assembly 50', which is illustrated for purposes of clarity only in association with the decorative visor, but could be used in association with any item, such as a mask, pouch, hat, headband, clothing item, etc., for securement to any article, such as a person's head or waist, or to any object or body part, includes a pair of extension segments 51' and 52'. The extension segments 51' and 52' are structured to extend along opposite sides of the article, such as the user's head, in order to maintain the item, namely the visor assembly 10" in the illustrated embodiment, effectively positioned on the user's head. In this embodiment of the securing assembly 50', the extension segments 51' and 52' of the rear securing region 50' are structured to be coupled with one another. Furthermore, as it is understood that user's having varying dimension heads may choose to wear a particular visor assembly 10", the securing assembly 50' of present invention is structured to have an elastic configuration which permits adjustable positioning and secure engagement of the extension segments 51' and 52' around heads of varying sizes. In particular, when in an uninflated orientation the normal characteristics of the first and second material panels 20 and 22 results in the extension segments 51' and 52' being generally inelastic. Due, however, to the precise and specific positioning of the interior seals 37, which define a series of chambers in the extension segments 51' and 52', an elastic configuration/characteristic is defined in the extension segments 51' and 52'. Specifically, the interior seals 37 are preferably disposed in generally aligned, spaced apart relation from one another, and thereby define a series of spaced apart chambers within an interior region between the extension segments 51' and 52'. Moreover, due to the positioning of the seals relative to one another, upon inflation of the interconnected chambers between the seals 37, the general elastic configuration of the extension segments 51' and 52' is achieved. For example, it is seen that due to the positioning of the interior seals 37, as the interconnected chambers are filled, a general contraction of the extension segments 51' and 52' is achieved. Still, however, as tension is applied to the ends of the extension segments 51' and 52', the air is displaced effectively throughout the preferably interconnected chambers in order to permit stretching of the extension segments 51' and 52' into a larger configuration. As a result, a snug and secure fit is maintained by the extension segments 51' and 52' about the article.

In order to couple the extension segments 51' and 52' with one another and maintain the item, namely the visor assembly 10", on the user's head, a fastening assembly is provided.

While the fastening assembly may include a number of varying, even adjustable configurations, such as a snap, adhesive, hook and loop fastener pad, magnet, clip, tie, etc., in the illustrated embodiment of the Figures, the fastening assembly includes a first fastener element 57 disposed on one of the extension segments 52' and a second fastener element 56 disposed on an opposite one of the extension segments 51'. In particular, the first and second fastener elements 56 and 57 are structured to be matingly interconnected with one another so as to maintain the visor assembly 10 securely positioned on the user's head. Furthermore, in the illustrated embodiment, the first fastener element 57 includes one or more apertures 58 defined therein. Correspondingly, the second fastener element 56 includes an enlarged configuration structured to extend through a corresponding aperture 58 of the first fastener element 57. In the embodiment shown, the second fastener element 56 includes an enlarged arrow-type configuration. Although when un-inflated the substantially non rigid configuration of the second fastener element 56 does not function to prevent its removal from the corresponding aperture 58 of the first fastener element 57, when inflated a generally rigid characteristic is provided in the second fastener element 56. Due to the generally arrowed configuration of the second fastener element 56, it is able to pass through the aperture 58 in the first fastener element 57, compressing slightly to permit introduction through the aperture 58. Once the second fastener element 56, however, extends completely through the aperture 58, the enlarged rear portion thereof resists removal and disengagement of the fastener means. In fact, affirmative compression of the second fastener element 56 is generally required in order to provide for effective removal thereof from the aperture 58 of the first fastener element 57. As a result, the integral and effective configuration of the fastener means can be provided with one another and/or the forward shading region of the visor assembly 10" of the present invention with the rear securing region 50' achieving an adjustable and secure fit. Furthermore, although as shown in the embodiment of the figures the extension segments extend from and are secured to the remainder of the visor assembly, they may be integrally or separately secured to any item so as to achieve securement thereof to an article, and if desired, the extension segments may be integral with one another and not necessarily with the item to be secured, so as to define a single element. In such an embodiment the item to be secured may be hooked or otherwise engaged with or by the extension segments.

It is also noted, as illustrate in FIG. 8, that the rear securing region 50" may include a pair of extension segments 51" and 52" formed of a flexible material, such as the material of the material panels in an unsealed form. Also, as in FIG. 9, one or more elastic straps 51'" may be utilized to define the rear securing region 50'".

It is also noted, that the interior seals provided in the decorative visor assembly 10 of the present invention, in addition to defining the forward shading region 40, the rear securing region 50, and the upwardly depending central region 60, also function to provide and define specific ornamental shapes and configurations in the visor assembly 10. For example, decorative patterns and three dimensional arrangement can be effectively achieved utilizing the interior seals to define a plurality of interior chambers within the primary chamber 25.

As previously indicated, although the visor assembly of the present invention may include merely a forward shading region 40 and rear securing region 50, as illustrated in FIG. 3, in the preferred embodiment, the interior seals further define an upwardly depending central region 60. In particular, the upwardly depending central region 60, which is structured to provide a further enhance visor configuration and also provide for decorative embellishment of the visor assembly 10, is defined by interior seals which are positioned such that upon the primary chamber 25 being inflated, the force of inflation that is translated through the first and second material panels 20 and 22 causes the upwardly depending region 60 to extend upwardly out of a plane of the forward shading region 40, and preferably into a generally perpendicular orientation. In the preferred embodiment, interior seals 28 are provided so as to essentially separate the upwardly depending region 60 from the forward shading region 40, thereby providing that the forces translated through the first and second material panel at the upwardly depending region 60 are isolated and focused to extend the upwardly depending region 60 out of the plane of the forward shading region 40. Moreover, it is preferred that the interior seals define a force focus segment 30. The force focus segment 30 is preferably vertically aligned and centrally oriented within the visor assembly, and is structured to draw in a plurality of the forces translated through the first and second material panels 20 and 22 in order to urge the upwardly depending region 60 out of the plane of the forward shading region 40 when the primary chamber is inflated. For example, as illustrated in FIG. 2, interior seals 32, 34 and 35 are all directed towards the force focus segment 30. As a result, when the primary chamber 25 is inflated, a contraction of forces towards the force focus segment 30 is achieved and the contraction and upward extension of the upwardly depending region 60 is attained. Such is similar to the case in FIG. 6 wherein the interior seals 32 and 34 are directed towards the force focus segment 30. Additionally, as indicated, it is preferred that the force focus segment 30 be vertically and centrally aligned within the visor assembly 10, essentially defining a central vertical axis of the visor assembly. Furthermore, in the preferred embodiment, the left and right sides of the visor assembly 10, relative to an axis defined by the force focus segment 30, are completely symmetrical with one another, thereby maintaining proper alignments and orientation of the forces once the primary chamber 25 is inflated and tension is exerted on the first and second material panels 20 and 22 as directed by the interior seals. It should also be noted, that as illustrated in FIG. 7, the force focus segment may include an interior channel 31 defined by at least two spaced, generally parallel seals 30'.

In addition to the generally attractive embellished appearance provided by the upwardly depending region 60, in the preferred embodiment, the upwardly depending region 60 further includes a central display area 62. The central display area 62 is structured and disposed to receive decorative indicia disposed thereon and thereby provide a clearly visible and centrally disposed region for ornamental display of logos, designs and other indicia. Lastly, it is noted that as indicated the interior seals are positioned in order to maintain symmetry about a central vertical axis of the visor assembly 10. Moreover, that symmetry and the positioning of the seals is such that complete reversibility of the visor assembly may be achieved, thereby providing multiple decorative appearances merely by varying the ornamental indicia and/or the manner in which the visor assembly 10 is positioned on the user's head.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Now that the invention has been described,

What is claimed is:

1. A decorative visor assembly comprising:
   a first, generally planar material panel and a second, generally planar material panel,
   a seal assembly structured to selectively and precisely couple said first material panel to said second material panel,
   said seal assembly including a perimeter seal structured to define a primary chamber between said first and said second material panels,
   said perimeter seal being substantially fluid impervious so as to contain a quantity of a fluid within said primary chamber,
   valve means structured and disposed to permit the selective flow of the fluid into said primary chamber so as to define an inflated orientation and a deflated orientation of said primary chamber, said seal assembly further including a plurality of interior seals, said interior seals coupling said first material panel to said second material panel such that upon inflation of said primary chamber, a force of inflation is precisely and selectively translated through said first and said second material panels so as to define a forward shading region and a rear securing region, and said rear securing region including a pair of extension segments, said extension segments being structured to extend along opposite sides of a user's head and be coupled with one another so as to extend said forward shading region outwardly, in a generally perpendicular orientation from a forehead of the user in a shading relation over a user's eyes.

2. A decorative visor assembly as recited in claim 1 wherein said interior seals which define said extension segments of said rear securing region are structured to define a series of spaced apart chambers within said extension segments, said chambers, when inflated, being structured to define an elastic configuration in said extension segments, thereby permitting said extension segments to securely engage heads of varying sizes.

3. A decorative visor assembly as recited in claim 2 wherein said extension segments include a plurality of said interior seals disposed in generally aligned, spaced apart relation from one another.

4. A decorative visor assembly as recited in claim 3 wherein said interior seals are disposed relative to one another such that upon inflation of said interconnected chambers said extension segments achieve said elastic configuration.

5. A decorative visor assembly as recited in claim 2 wherein said plurality of spaced apart chambers of said extension segments are interconnected with one another.

6. A decorative visor assembly as recited in claim 1 wherein said extension segments further include fastening means structured and disposed to couple said extensions segments with one another about the user's head.

7. A decorative visor assembly as recited in claim 6 wherein said fastening means includes a first fastener element disposed on one of said extension segments and a second fastener element disposed on an opposite one of said extension segments, said first and said second fastener elements being structured to be matingly interconnected with one another.

8. A decorative visor assembly as recited in claim 7 wherein said first fastener element includes an aperture defined therein and said second fastener element includes an enlarged configuration structured to extend through said aperture of said first fastener element and resist facilitated removal thereof when inflated.

9. A decorative visor assembly as recited in claim 1 wherein said interior seals further define an upwardly depending central region upon said primary chamber being inflated, said interior seals which define said upwardly depending central region being disposed such that said force of inflation that is translated through said first and said second material panels causes said upwardly depending central region to extend upwardly out of a plane of said forward shading region.

10. A decorative visor assembly as recited in claim 9 wherein said upwardly depending region includes a central display area structured and disposed to receive decorative indicia disposed thereon.

11. A decorative visor assembly as recited in claim 1 wherein said first material panel and said second material panel are formed of a flexible, yet generally inelastic material such that the forces translated therethrough are properly directed by a positioning of said interior seals.

12. A decorative visor assembly as recited in claim 1 wherein said interior seals are symmetrically disposed about a central vertical axis of the visor assembly.

13. A decorative visor assembly as recited in claim 1 wherein said interior seals are disposed in said first and said second material panels so as to permit reversibility of the visor assembly.

* * * * *